United States Patent [19]

de la Cruz

[11] 4,350,647

[45] Sep. 21, 1982

[54] PERMANENT ADAPTER FOR A MEDICAL HUMIDIFIER

[75] Inventor: Exequiel de la Cruz, Palatine, Ill.

[73] Assignee: Respiratory Care, Inc., Arlington Heights, Ill.

[21] Appl. No.: 275,220

[22] Filed: Jun. 19, 1981

[51] Int. Cl.³ .................. B01F 3/04; A61M 15/00
[52] U.S. Cl. .................. 261/65; 128/200.11; 128/205.23; 137/859; 261/121 R
[58] Field of Search ............... 261/65, 78 A, 121 R, 261/DIG. 65; 137/859; 128/200.11, 200.18, 200.21, 205.23

[56] References Cited

U.S. PATENT DOCUMENTS

| 3,807,445 | 4/1974 | McPhee | 261/DIG. 65 |
| 3,903,884 | 9/1975 | Huston et al. | 261/DIG. 65 |
| 4,039,639 | 8/1977 | Kankel et al. | 261/DIG. 65 |
| 4,061,698 | 12/1977 | Thornwald | 261/DIG. 65 |
| 4,100,235 | 7/1978 | Thornwald | 261/DIG. 65 |
| 4,134,940 | 1/1979 | Sherman | 261/DIG. 65 |
| 4,149,556 | 4/1979 | Schwabe | 261/DIG. 65 |
| 4,190,046 | 2/1980 | Virag | 261/DIG. 65 |
| 4,223,842 | 9/1980 | Hayes | 261/DIG. 65 |

Primary Examiner—Richard L. Chiesa
Attorney, Agent, or Firm—Eric P. Schellin

[57] ABSTRACT

An adapter for connection between an oxygen flowmeter and a water bottle whose contents humidify oxygen fed to a patient. An audible duckbill valve is mounted on a valve seat transverse to the longitudinal axis of the connector. When oxygen pressure through the connector becomes excessive, the valve opens, producing an audible sound to alert an attendant to the condition.

6 Claims, 4 Drawing Figures

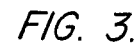
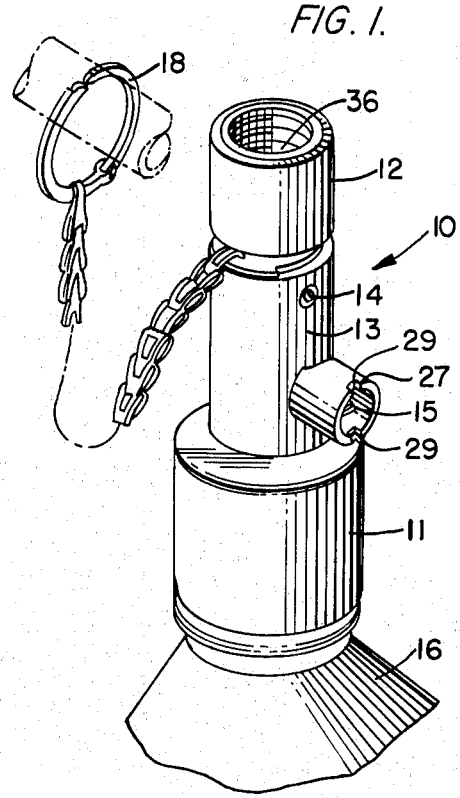
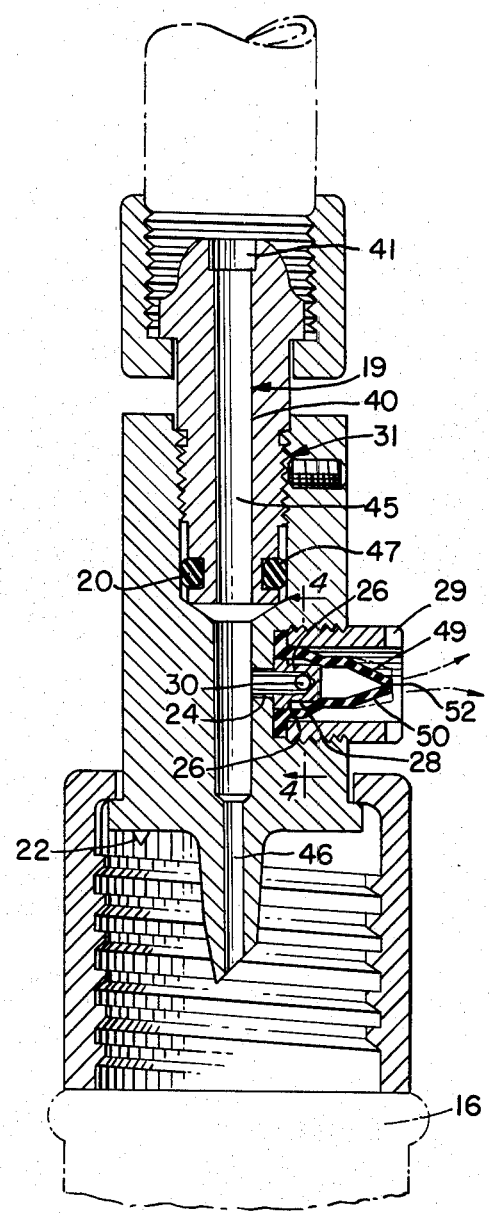
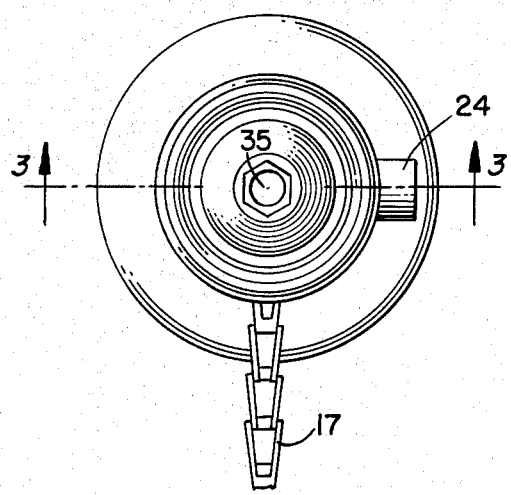
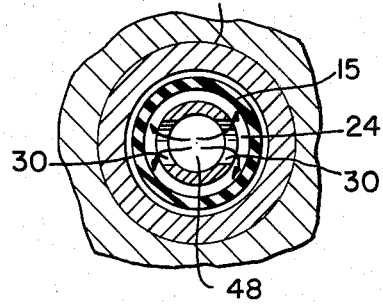

PERMANENT ADAPTER FOR A MEDICAL HUMIDIFIER

BACKGROUND OF THE INVENTION

The present invention relates to an adapter for a humidifier used in respiratory apparatus.

Inhalation therapy is frequently used for patients suffering from such diseases as emphysema, stroke, heart stoppage, drowning, and a variety of other applications which require the administration of either pure oxygen or a high percentage of oxygen or other medicaments administered through inhalation therapy. Humidifiers are employed in the respiratory apparatus. The patient inhales a gas-liquid mixture from the humidifier, which is effective in moistening the gas that is passed through the humidifier and discharged therefrom in a manner to introduce the moistened gas, such as oxygen or air, into a person's respiratory system. The gas is humidified so as to prevent dessication of the respiratory tract or membranes during treatment over a prolonged period of time.

There has been a problem in the past with medical humidifiers in reliably determining when humidified gas was inadvertently cut off from the patient. This often happened when the oxygen tube leading to the patient's mask became kinked. Thus, while it appeared that the patient was still receiving the oxygen or other humidified gas, he was in effect cut off from his inhalation therapy treatment.

It has been proposed to use various check valves or pressure relief valves in a humidifier to avoid an excessive pressure buildup that might break tubing joints, etc. from their connections. When such a pressure relief valve does open to release pressure, it is important that the attending medical personnel be aware of it. This is so he can correct the obstruction causing the pressure buildup and quickly get the patient back on his prescribed inhalation therapy. Previous inhalation therapy apparatus involved a spring biased check valve that exhausted released gas into a knife edge whistle such as a common toy whistle. However, the gas flow rates in a medical humidifier are sometimes too slow to cause a noise with such a whistle. Also, at very low pressures of between 2 and 4 psi above atmospheric, these knife edge whistles do not always operate reliably.

U.S. Pat. Nos. 4,061,698 and 4,100,235 disclose humidifier-nebulizer apparatus having an adapter head that includes control valve means movable to discharge a nebulized gas-liquid mixture from the adapter head during a nebulizing mode of operation and adjustable to introduce liquid oxygen into the reservoir in a manner to effect discharge of humidified oxygen through a discharge port of the liquid reservoir of the apparatus. However, these apparatus do not include an audible relief valve means which serves as an audible alarm to indicate an above normal pressure in the humidifier to alert an attendant of his condition.

Sherman, U.S. Pat. No. 4,134,940, discloses a humidifier adapter comprising two oppositely facing, independently movable, internally threaded pieces for connection to the gas conduit and the water bottle, a body piece intermediate the two end pieces with an axial hose for holding a spike, a set screw transfixing the body piece, two pressure sealing "O" rings, and an audible duck bill valve with retaining screw and flange upon which the valve sits. An internal pressure chamber is located between the spike and internal diameter of the body piece which connects with the water bottle, which body piece is transfixed by the duck bill valve.

Kankel et al, U.S. Pat. No. 4,039,639, discloses a humidifier comprising a flap valve for emitting an audible alarm when excessive pressure exists in a nebulizer device. A flexible tube is used to connect an oxygen diffuser immersed in liquid to a source of oxygen.

McPhee, U.S. Pat. No. 3,807,445, discloses an audible pressure relief valve for a medical humidifier. The valve has a rubber disc that is dimensionally tuned to vibrate against a valve seat and emit an audible sound at gas flow rates of 3 to 15 liters per minute and pressures of 1 to 5 psi above atmospheric pressure.

Ollivier, U.S. Pat. No. 3,867,934, discloses a pressure monitor for use with a lung ventilator. The monitor is connected to a pneumatically-operated warning device which may be audible, visible, or both.

Adolphsen et al, U.S. Pat. No. 2,267,009, discloses an oxygen inhaling assembly including a tube for oxygen flow. If the tube becomes clogged, pressure will build up in a casing and a diaphragm connected to the casing will begin to lift, releasing gas from the casing for passage through a duct to the atmosphere. In this case, the diaphragm will vibrate, emitting a sound similar to that of an air horn.

SUMMARY OF THE INVENTION

An adapter is provided for connection between an oxygen flowmeter and a water bottle whose contents serve to humidify the oxygen being fed to a patient. The connector comprises two oppositely facing, independently movable, internally threaded cups, one for connecting to a gas conduit, the other to the water bottle. A body piece intermediate of the two cups holds a sealing pin which is also held by a set screw and which impinges upon an "O" ring. An audible duck bill valve is mounted on a valve seat transverse to the longitudinal axis of the connector. A retainer holds the valve in place; when the oxygen pressure through the valve becomes excessive, the valve opens, producing an audible sound to alert an attendant to the condition. The entire connector may be hung on a chain which has a snap clip retaining ring at one end to facilitate connection to a pipe between uses.

DESCRIPTION OF THE DRAWINGS

FIG. 1 is a front view of the adapter of the present invention shown attached to a pre-filled water bottle.

FIG. 2 is an end view and a cross-sectional view taken along line 3—3 of FIG. 1 showing the flowmeter connector end view of the adapter of the present invention.

FIG. 3 is a longitudinal cross-sectional view of the adapter of the present invention attached to a pre-filled water bottle and to a gas conduit.

FIG. 4 is a cross-sectional view of the cross T of the adapter showing the cross T, the duckbill valve, and the retainer.

Referring to the drawings, and particularly to FIG. 1, the adapter according to the present invention is shown at 10. The adapter is generally of cylindrical shape, having a lower cup 11 of larger diameter than the body piece 13 and upper cup 12. A generally coaxial bore 36 is provided internally of the adapter and extends the entire length of the body of the adapter. Lower cup 11 is internally threaded for connection to a respirator bottle or liquid container or reservoir 16. The bottle 16 is constructed to contain a quantity of purified or sterile liquid, such as water, and has provision for mounting the adapter 10 thereon. In operation, the adapter 10 is connected at upper cup 12 to a flowmeter (not shown) which in turn is connected to a source of oxygen, air, or the like (not shown). Upper cup 12 is internally threaded.

The body piece 13, intermediate the upper cup and the lower cup, contains a duckbill valve 15 within a retainer 27 which holds the duckbill valve in place. The body piece 13 also holds a set screw or sealing pin, shown at 14. Attached to the body piece 13 is a chain 17 with a snap clip retaining ring 18 to facilitate connection of the adapter to a pipe (shown in dotted lines) between uses.

FIG. 2 shows a horizontal cross-section of the adapter 10. The hole through sealing pin member 19 is shown at 35, the retainer for the duckbill valve at 27, and the retaining chain at 17.

FIG. 3 shows a longitudinal cross-section of adapter 10 in place upon bottle 16. The bottle, or liquid reservoir, generally is formed of blow-molded polyethylene and is sealed by a pierceable membrane. To connect the adapter to the bottle, the lower cup 11 of the adapter is screwed over the top of the bottle 16 by means of the internal threads in the lower cup 11. Annular scoring member 22, located at the bottom of body piece 13, scores the top of the membrane on the bottle 16 to produce a tight seal between the bottle and the adapter.

The adapter 10 is provided with sealing pin member 19 in a seated, snug relation longitudinally of the entire adapter. The sealing pin member 19 includes a generally tubular body 40 and sealing head 41. The sealing head 41 is adapted to mate with, for example, a seal in a flowmeter (not shown). The sealing pin member 19 centrally terminates in a cross T 24 with holes 30 on either side of the stem of the cross T to allow escape of built-up gas. Shoulders 26 of the cross T 24 hold the duckbill valve 15 in place. A retainer 27 is screwed into female threads 28 on the cross T to hold the duckbill valve 15 in place. Notches 29 on the retainer 27 enable the retainer to be screwed on with a screwdriver. "O" rings 20 assist in providing a tight seal of the adapter. The "O" ring shown at 20 is located in a ring groove 47 in the mid portion of the sealing pin member 19. The ring groove 47 may be made in any suitable manner in accordance with generally known machining principles. Set screw 14 on the body piece 13 is provided so as to be tightenable against thread 31 of the adapter to prevent unwanted rotation of the sealing pin member 19 after it is properly seated.

The sealing pin member 19 includes at least two stepped diameter portions. As illustrated in FIG. 3, a large diameter portion 45 of the tubular body extends through the upper cup 12 and the body piece 13, and a small diameter through the spike end portion 46 extends through the lower cup 11 of the adapter.

FIG. 4 is a cross-section of cross T 24 showing holes 30 on either side of the stem of the cross T allowing escape of built-up gas. Duckbill valve 15 surrounds the cross T, and the retainer 27 surrounds the duckbill valve.

The tubular body 40 of the sealing pin member defines a longitudinal internal passage which may be in the form of a constant-diameter bore. This passage serves as a conduit for the pressurized gas through the adapter 10 to allow the gas to pass through the bottle 16 for moistening before discharge into a cannula.

In order to relieve excess pressure in the adapter, the spike member 13 is provided with a cross T 24 which communicates with the longitudinal internal passage of the spike member. The cross T defines an internal passage 48 at right angle to the longitudinal internal passage of the spike member and establishes communication between the longitudinal internal passage and the internal passage of the cross T. Two openings or port means 30 on the cross T establish communication between the internal passage of the cross T and the outside atmosphere. When the duckbill valve 15 is mounted on the cross T, air escaping from the openings 30 will activate the duckbill valve. The two opposing tapered sides or valve portions 49 and 50 of the duckbill valve are flexible and vibratable and converge to an apex where the two sides define a slit 52 between them. Normally this slit is closed as the two opposing sides lie flat against each other at the apex. When there is gas pressure, however, these portions separate and allow a gas discharge through the slit. These wall portions are adapted to vibrate and produce an audible signal when gas flows between them.

The adapter of the present invention is reusable and permanent. The adapter is preferably metallic and is made, for example, by machining suitable material, such as brass. All such brass parts are then preferably covered with a chrome plate or suitable stainless steel. The set screw 14 may be stainless steel. The "O" ring and the duckbill valve are preferably made from a silicone rubber having the ability to withstand temperatures normally experienced in a steam autoclave, such as 250° F. to 275° F., for thirty minutes. Preferably, the material will withstand temperatures of 400° F. or more. An example of such material is a 45 durometer methyl-vinyl siloxane polymer proceesed for use in external medical equipment. This construction allows the adapter 10 to be sterilized as needed.

In operation, the adapter 10 as described herein will be used as part of respiratory apparatus to humidify a gas in inhalation therapy. If pressure rises above normal in the respirator bottle or liquid reservoir 16, for any reason, the adapter 10 will serve as an audible alarm to attract the attention of an attendant who can inspect the apparatus and remove the cause of the high pressure. If the pressure in the respirator bottle is high as a result of high pressure from the gas source, globules of water may form and exit the humidifier apparatus, and enter the lungs of the patient. On the other hand, if high pressure in the respirator bottle results from an occlusion in the outgoing line, such as by pinching of the line, humidified gas may not reach the lungs at all. In either situation, the result is a malfunction and an attendant should make an appropriate remedial adjustment.

Accordingly, gas flow exceeding a predetermined pressure is audibly vented to the atmosphere through the duckbill valve 15. In a device constructed in accordance with the illustrated embodiment, the audio range has been found to be effective from about 0.07 cfm to about 0.5 cfm.

One adapter has been constructed in which the adapter body is approximately two inches long and has a hose portion of approximately 0.40 inch. The large bore diameter portion of the spike member 13 has a diameter of approximately 0.125 inch. The material for the adapter body and the spike member is chrome plated brass. The set screw 14 is a socket type screw made of stainless steel. The duckbill valve is made of rubber having the same characteristics described earlier in connection with the O-ring.

Generally, the gas flow through the adapter 10 and the bottle 16 to the patient ranges from approximately two liters per minute to approximately fifteen liters per minute, i.e., from about 0.07 cfm to about 0.53 cfm. In the aforesaid construction, an internal pressure buildup of 3 to 3.5 psig will cause an outward flow of about 0.007 cfm through the duckbill valve 15. Such pressure buildup might result, for example, from a kink or other obstruction in the cannula leading to the patient. In accordance with this invention, the duckbill valve 15 is effective to respond to such low gas flow of about 0.07 cfm by an audible vibration of the opposing wall portions 49 and 50. This audible vibration of these opposing walls continues until the flow of gas outwardly of the duckbill valve exceeds about 0.5 cfm. In terms of liters per minute, this means that the valve audibly vibrates at gas flow rates therethrough within a range of from two to fifteen liters per minute. At gas flow rates exceeding fifteen liters per minute, the opposing wall portions 49 and 50 remain separated without audibly vibrating as the gas flows therebetween. The flow of fifteen liters per minute (about 0.53 cfm) at the upper end of the audible range results from a pressure in the respirator bottle 16 of about 6.5 psig.

Thus, audible vibrations are produced in the duckbill valve 15 at internal pressures of 3 to 6.5 psig at gas flow rates of two to fifteen liters per minute. An audible signal will be provided to alert an attendant to the fault conditions so that corrective action can be taken and the patient can again receive moistened gas from the system.

In summary, there has been disclosed a permanent humidifier adapter 10 for mounting on an engageable portion of a container or liquid reservoir 16 over a pierceable sealed surface of the container. A supply of purified or sterile water is sealed in the container. The adapter also connects a pressurized gas tube to the container for introducing gas with the supply of water to moisten or humidify the gas. The adapter 13 includes an upper cup means 12, a body piece 13, and a lower cup means 11, the lower cup 11 having means at one end for engaging the container, and a bore axially extending through the adapter. A spike member 13 is provided and inserted within the adapter. The spike member has a generally tubular body. A cross T 24 establishes communication between the inside passage of the spike member through which gas enters the container, and the outside atmosphere. An audible relief valve means including a duckbill valve is located on the cross T, which valve means effects audible pressure relief of the adapter under normal pressure chamber under above normal pressure conditions. The illustrated audible relief valve means has an effective audible range from the minimum flow that establishes sound to approximately eight times such minimum flow.

Although the invention has been described in connection with a preferred embodiment, alternatives, modifications, and variations may be apparent to those skilled in the art of the foregoing description. Accordingly, it is intended to embrace all such alternatives, modifications, and variations as fall within the spirit and scope of the appended claims.

What is claimed is:

1. A permanent adapter for mounting on an engagable portion of a container over a pierceable seal thereon sealing therein a supply of purified or sterile water, and to be connected to a pressurized gas tube for introducing gas into the supply of water to moisten the gas, the adapter comprising:
    a. two oppositely facing cups, an upper cup for connection to a gas conduit, a lower cup for connection to a container;
    b. a body piece intermediate the oppositely facing cups;
    c. an axial bore through the adapter;
    d. a spike member for assembly within the adapter, the spike member having a tubular body defining a gas passage therein;
    e. relief means in the tubular body of the spike means establishing communication between the gas passage and the outside atmosphere, the relief means being a cross T having a tubular body defining a second gas passage therethrough which is perpendicular to the gas passage of the spike means; said second gas passage extending directly outwardly from the gas passage of the spike means to the relief means;
    f. audible relief valve means located in the relief means to effect audible pressure relief of the gas passage under above normal pressure conditions.

2. An adapter according to claim 1 wherein the cups, the body piece, and the spike member are made of brass having chrome plate surfaces, or suitable stainless steel and having machine finish.

3. An adapter according to claim 1 wherein the audible relief valve means includes an audible duckbill type flexible valve.

4. An adapter according to claim 3 wherein the duckbill type valve is made of a silicone rubber capable of with standing temperatures normally experienced in a steam autoclave.

5. An adapter in accordance with claim 3 wherein the duckbill valve has an audio range effective with gas flows therethrough of from two to fifteen liters per minute.

6. An adapter in accordance with claim 1 wherein a chain with a retaining ring is attached to the body piece.

* * * * *